US010522324B1

(12) United States Patent
Giannuzzi

(10) Patent No.: US 10,522,324 B1
(45) Date of Patent: Dec. 31, 2019

(54) METHOD OF PRODUCING LIFT OUT SPECIMENS FOR TEACHING, PRACTICE, AND TRAINING

(71) Applicant: EXpressLO LLC, Lehigh Acres, FL (US)

(72) Inventor: Lucille A. Giannuzzi, Fort Meyers, FL (US)

(73) Assignee: EXpressLO LLC, Lehigh Acres, FL (US)

( * ) Notice: Subject to any disclaimer, the term of this patent is extended or adjusted under 35 U.S.C. 154(b) by 0 days.

(21) Appl. No.: 16/052,788

(22) Filed: Aug. 2, 2018

(51) Int. Cl.
| | |
|---|---|
| *G01N 1/00* | (2006.01) |
| *H01J 37/20* | (2006.01) |
| *H01J 37/26* | (2006.01) |
| *H01J 37/305* | (2006.01) |
| *H01J 37/31* | (2006.01) |
| *G01N 1/32* | (2006.01) |

(52) U.S. Cl.
CPC ........... *H01J 37/26* (2013.01); *G01N 1/00* (2013.01); *G01N 1/32* (2013.01); *H01J 37/20* (2013.01); *H01J 37/3056* (2013.01); *H01J 37/31* (2013.01); *H01J 2237/3109* (2013.01); *H01J 2237/31745* (2013.01)

(58) Field of Classification Search
CPC ........ G01N 1/00; H01J 37/26; H01J 37/3056; H01J 37/20; H01J 37/31; H01J 2237/31745; H01J 2237/201
See application file for complete search history.

(56) References Cited

U.S. PATENT DOCUMENTS

| | | | |
|---|---|---|---|
| 6,420,722 B2 | 7/2002 | Moore et al. | |
| 6,570,170 B2 | 5/2003 | Moore et al. | |
| 6,799,959 B1 * | 10/2004 | Tochimoto | B29C 41/12 425/130 |
| 7,041,985 B1 | 5/2006 | Wang et al. | |
| 8,134,124 B2 | 3/2012 | Blackwood et al. | |
| 8,357,913 B2 | 1/2013 | Agorio et al. | |
| 8,455,821 B2 | 6/2013 | Arjavac et al. | |

(Continued)

OTHER PUBLICATIONS

Giannuzzi et al., Microsc. Microanal. 21, 1034-1048, 2015.

(Continued)

*Primary Examiner* — Wyatt A Stoffa
(74) *Attorney, Agent, or Firm* — Schaffer IP Law, LLC

(57) ABSTRACT

A method for creating a low-cost specimen used for training users in lift out techniques is prepared using additive manufacturing. This replaces the more expensive and time-intensive subtractive manufacturing methods traditionally used that operate by milling or ablation with charged particle focused ion beam (FIB) instruments or lasers. The method comprises building up a sample from a substrate surface using additive manufacturing, building up trench walls within the sample that frame a trench using additive manufacturing, and building up a specimen between the trench walls using additive manufacturing. In a preferred form, the specimen has a shape taken from the group consisting of a lamella, a rectangular cuboid, a triangular prism, and a regular prism. Tabs and other support structures may be eliminated using subtractive milling or chemical dissolving methods to create a freestanding specimen separate from the trench.

10 Claims, 15 Drawing Sheets

(56) References Cited

U.S. PATENT DOCUMENTS

| | | |
|---|---|---|
| 8,525,137 B2 | 9/2013 | Blackwood et al. |
| 8,740,209 B2 | 6/2014 | Giannuzzi |
| 8,789,826 B2 | 7/2014 | Giannuzzi |
| 8,884,247 B2 | 11/2014 | Miller et al. |
| 8,890,064 B2 | 11/2014 | Arjavac et al. |
| 9,275,831 B2 | 3/2016 | Arjavac et al. |
| 2010/0032581 A1 | 2/2010 | Grosse et al. |
| 2015/0270088 A1* | 9/2015 | Satoh ............... B23K 15/002 |
| | | 315/107 |
| 2016/0356683 A1* | 12/2016 | Krause ................ G01N 1/44 |
| 2016/0368077 A1* | 12/2016 | Swaminathan ....... B25J 9/0096 |
| 2017/0199104 A1* | 7/2017 | Gradinaru ............. G01N 1/30 |
| 2018/0363104 A1* | 12/2018 | Fujieda ............... F04D 17/10 |
| 2019/0047049 A1* | 2/2019 | Fujieda ............... B33Y 10/00 |

OTHER PUBLICATIONS

Langford et al., J.Vac. Sci. Technol. B, 19. 755-758, 2001.
Thompson et al., Ultramicroscopy, 107, 131-139, 2007.
Maruo et al., Three-dimensional Microfabrication with Two-Photo-Absorbed Photopolymerization, Optics Letters, vol. 22, Issue 2, 132-134, 1997.

* cited by examiner

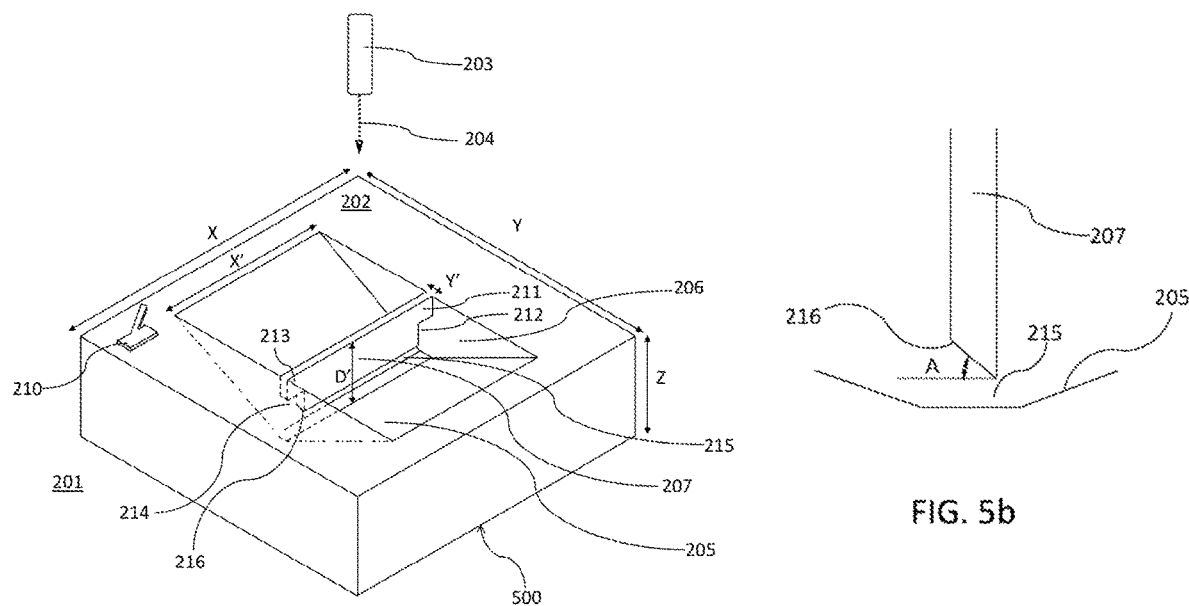
FIG. 5a
FIG. 5b
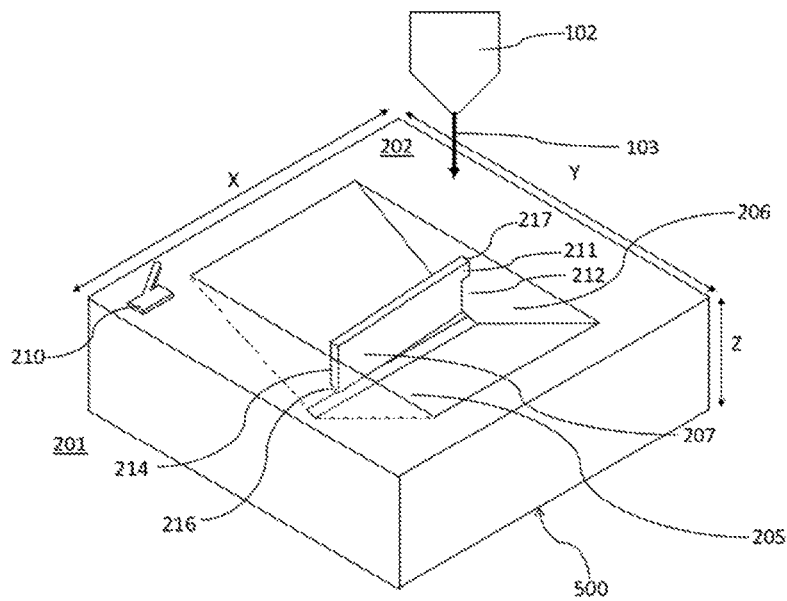
FIG. 5c

U.S. 10,522,324 B1

METHOD OF PRODUCING LIFT OUT SPECIMENS FOR TEACHING, PRACTICE, AND TRAINING

BACKGROUND OF THE INVENTION

1. Field of the Invention

This disclosure relates to detailed methods to create site specific specimens using additive manufacturing (e.g., AM), also known as three-dimensional (3D) printing or rapid prototyping, rather than conventionally prepared specimens that use material removal via milling or ablation methods such as with a charged particle focused ion beam (FIB) instrument or laser. The specimens produced via AM may be similar to or identical in geometry to FIB prepared specimens, but are less expensive to fabricate, and therefore can be used to teach or train users on the methods of FIB specimen preparation, FIB micromanipulation, and the so-called lift out specimen removal and micromanipulation techniques, while minimizing expensive FIB instrument usage.

2. Description of the Prior Art

Previous inventions by applicant (U.S. Pat. Nos. 8,740,209 and 8,789,826; and U.S. Pat. Ser. No. 62/533,468) describe a specimen carrier and methods of ex situ lift out (EXLO) from focused ion beam (FIB) prepared specimens for subsequent scanning/transmission electron microscopy (S/TEM) or other site-specific analysis of the extracted specimen (i.e., the EXpressLO method). These previous two patents (U.S. Pat. Nos. 8,740,209 and 8,789,826) describe a specimen carrier and methods used in conjunction with standard conical needle-shaped glass micromanipulator probes conventionally used for EXLO.

As per the previous inventions described by applicant, the EXpressLO method and apparatus allows for positioning the specimen in any orientation for optimized analysis of cross-sectioned specimens, plan view specimens, or for the so-called backside specimen placement. This inventive method has been found to reduce or eliminate FIB milling or laser ablation curtaining artifacts during subsequent processing using an asymmetric FIB milled cut to identify the specimen orientation.

A recent publication reviewed the adhesion forces responsible for EXLO (see Giannuzzi et al., 2015). While electrostatic forces were previously believed to control the lift out, the manipulation process, and adhesion to any carrier surface (e.g., the EXpressLO grid or a carbon coating on a three-millimeter grid), it was recently determined that in fact Van der Waals forces were primarily responsible for picking the specimen up and out of the FIB trench, as well as securing it to a carbon support film or EXpressLO carrier grid surface (see Giannuzzi et al., 2015). Additionally, the applicant's work discussed the use of beveled probe tips to optimizing Van der Waals for both specimen extraction (e.g., "lift out"), and manipulation via site specific placement to conventional thin-film coated grid carriers or previously patented specimen carriers (U.S. Pat. Ser. No. 62/533,468). The specimen fabrication described in this application may be used in conjunction with the EXpressLO patents above.

It can take hours, weeks, or years to master FIB specimen preparation and, in particular, FIB lift out methods. In each case, training new users requires numerous hours of expensive FIB time for milling specimens needed for training, teaching, execution, and practice of the lift out procedures. After FIB milling, the specimens may be extracted for analysis inside of the FIB using the so called in situ lift out (INLO) method or outside of the FIB using ex situ lift out (EXLO) or EXpressLO methods. It is generally well known that INLO takes both longer to perform and master, while EXLO is faster to perform and master. In either case, the techniques require tens, hundreds, or thousands of hours of practice and training to acquire proficiency necessary for high throughput success rates. More importantly, an expensive FIB instrument is needed to mill lift out specimens that may take on various shapes and geometries depending on the application. For example, a lift out specimen may be shaped (1) as a "lamella" or rectangular cuboid for analysis of cross-sections or monolithic materials, (2) as a "toblerone-shaped" chunk or triangular prism for "total release" or atom probe tomographic analysis, or (3) as a wedge-shaped rectangular prism for plan view specimens, and more. These three-dimensional shapes may also contain one or more tabs of material to hold the specimen in place prior to lift out. Each shape requires slightly different lift out methods which are well known.

Lift out specimens are usually prepared by charged particles instruments such as a focused ion beam (FIB) microscope or via laser ablation. This technique requires material removal by ion milling via physical sputtering or ablation such that only the region of interest remains intact and left behind as detailed below.

The usual start for any FIB lift out specimen is the preparation of a lamella or rectangular cuboid specimen as shown in FIGS. 1a-1i. Any FIB specimen geometry may optionally start with a particle beam induced deposition layer (e.g., C, Pt, W or other material) to denote and protect the underlying region of interest. For simplicity, this protective layer is left out of the figures described below. FIG. 1a shows a sample surface 101 that has been FIB milled using a FIB column 102 emitting energetic ions 103 to sputter and mill away material to produce a trench floor 104 and sidewall 105 and reveal the beginning of eventual lamella specimen 106. In FIG. 1b, the ion beam 103 is used to mill and remove material on the reverse side of lamella specimen 106 creating a similar trench floor 104 and trench sidewall 105. In FIG. 1c, the FIB is further used to remove material from either side of lamella specimen 106, until the desired thickness is achieved for specimen 106 as per FIG. 1d.

From the configuration shown in FIG. 1d, numerous types of FIB undercuts may be performed for various types of lift out specimens which requires tilting the sample approximately 45 degrees into the ion beam 102 as per FIGS. 1e and 1h. In FIG. 1e, the sample is tilted with respect to the FIB column 102 and the ion beam 103 is used to undercut the specimen using a "J-shaped" mill cut (collectively spaces 108, 109, and 110) and material removal as viewed from the ion beam. This J-cut results in a single tab of material 107 holding specimen 106 to trench sidewall 105 while removing material 108 under the tab 107. In addition, this creates an open region and material removal 109 under specimen 106, and material removal 110 on the side of the specimen 106 opposite tab 107. This resulting configuration shown in FIG. 1e is generally used for subsequent in situ lift out (INLO) or micro-sampling as shown by FIGS. 1f-1g with the sample tilted back at normal incidence to the ion beam. This "J-cut" is also the prelude to producing an ex situ lift out specimen as described below FIG. 1f shows steps associated with INLO where a probe 111 is mounted such that it can be inserted under vacuum in the charged particle instrument. Once inserted, the probe 111 is moved near to or touching specimen 106 and attached to specimen 106 using charged particle induced deposition 112 (e.g., C, W, Pt, etc.). Once the probe 111 is securely attached to specimen 106, tab 107 can be milled away such that the specimen is completely freed from its trench as per FIG. 1g, supported only by probe 111. Probe 111 retaining specimen 106 can be retracted and deposited onto a suitable carrier for additional FIB processing.

In another processing method, and after the FIB processing shown in FIG. 1d, the sample may be tilted ~45 degrees into the FIB column 102 and ion milled using beam 103 producing the so-called "U-shaped" undercut mill (collectively spaces 108, 109, and 110) as shown in FIG. 1h. The "U-cut" produces two tabs of material (e.g. tabs 107 and 113), holding specimen 106 to trench sidewalls 105 and surrounded by free space 108, 109, 110. After undercutting, the sample is generally tilted back to normal incidence or near normal incidence to FIB thin specimen 106 to its desired thickness and to remove any redeposited material accumulating on specimen 106 during the undercut operation. The material tabs may be FIB milled away as per FIG. 1i, leaving an asymmetric lamella-shaped specimen 106 completely FIB milled free and fully released from the trench sidewall 105 with free space 114. In FIG. 1i, the specimen 106 has been milled free using an asymmetric undercut, remaining nearly vertical by Van der Waals force attraction of the specimen edges with the trench walls 105. The specimen geometry in FIG. 1i is generally used for ex situ lift out specimen (EXLO) and EXpressLO methods described previously be the inventor of this application.

FIG. 2a shows the front side milling operation of a "toblerone" wedge-shaped or triangular prism geometry 120 typically FIB milled for atom probe tomography specimen preparation and subsequent in situ lift out (Thompson et al., 2007). Specimen 120 is FIB milled using FIB column 102 and ion beam 103 at angle ~1-45 degrees from the sample normal surface 101 creating trench floor 104 and trench sidewalls 105. In FIG. 2b, the sample is tilted in the opposite direction by the same amount shown in FIG. 2a to remove material with FIB column 102 and ion beam 103 to create a wedge-shaped specimen 120. In FIG. 2c the wedge-shape triangular prism specimen 120 has been additionally FIB milled at normal incidence to release one end 121 for subsequent INLO. The INLO method similar shown in FIG. 2d shows probe 111 attached to specimen 120 with deposition layer 112 and releasing the specimen for lift out by FIB milling away material as indicated by the free space 122.

FIG. 3a shows FIB milling with the sample surface 101 tilted ~45 degrees with respect to the FIB column 102 and ion beam 103 to create the beginning of a regular prism geometry specimen 130 generally used for plan view specimen preparation and subsequent lift out (Langford et al., 2001). FIB milling occurs below surface 101 to produce trench floor 104 and sidewalls 105. In FIG. 3b, the sample is tilted ~45 degrees in the opposite direction with respect to the FIB column 102 and ion beam 103 to produce specimen 130 attached by a tab of material 131 on one side of the specimen. The space 132 between an end of specimen 130 and the adjacent trench sidewall 105 is created by FIB milling away material from specimen 130. Specimen 130 may be manipulated via INLO as per FIG. 3c using probe 111 and deposit 112 and FIB milling tab 131 to create free space 133 separating the specimen 130 from its trench sidewall 105. This regular prism specimen 130 may also be manipulated by EXLO methods if the FIB is used to mill free tab 131 to create space 133 as per FIG. 3d. In FIG. 3d, specimen 130 may shift slightly and settle into the bottom of the trench, but the trench floor 104 and sidewall 105 will generally keep the specimen orientation "upright" such that it can be lifted out successfully.

Each specimen prepared by this "subtractive" prior art above may take tens of minutes to an hour or more of FIB instrument preparation time (excluding any INLO steps). Thus, and with FIB instrument time being so valuable, a more efficient method for producing samples is required that fulfills the need for training, teaching, execution, and practice.

SUMMARY OF THE INVENTION

It has been discovered that the creation of specimens having geometries usable to train operators of focused ion beam (FIB) instruments and methods can be accomplished by additive manufacturing (AM) or three-dimensional (3D) printing, which may take minutes or even seconds to manufacturing using a less expensive instrument to purchase and maintain. By pre-manufacturing these shapes without an expensive FIB, training, education, execution, and practice can occur more easily and with greater repetition at a faster rate and at less cost.

Site specific specimens are formed using additive manufacturing (e.g., AM), also known as three-dimensional (3D) printing, or rapid prototyping, rather than conventionally prepared specimens using material removal via milling or ablation methods such as with a charged particle focused ion beam (FIB) instrument or laser. The specimens produced via AM may be similar to or identical in geometry to FIB prepared specimens, but are less expensive to fabricate, and therefore, can be used to teach or train users on the methods of FIB specimen preparation, FIB micromanipulation, and the so-called lift out specimen removal and micromanipulation techniques, while minimizing expensive FIB instrument usage. The 3D printed specimens which mimic FIB specimens can be used for teaching, training, and practice of lift out methods through repetition for success and proficiency of lift out methods.

Any AM process with sufficient resolution may be used to make the lift out specimens from any material (e.g., metal, ceramic, polymer, or composite). The AM process presently under consideration utilizes a commercially available laser two-photon polymerization (TPP) technique that can create 3D nano-structures in a polymeric photoresist or resin in just seconds. The photoresist may be conductive or non-conductive. A computer model of the lift out specimen is designed and printed to produce a 3D structure extending above the substrate surface. In the TPP technique, a single laser is pulsed and focused into photoresist causing the absorption of two or more photons. The laser beam itself can be scanned in x,y in combination with x,y stage motion. The beam can be focused at different heights (z) to create 3D structures. The negative resist that is not polymerized via the laser is dissolved in a developer solution and rinsed away.

Alternatively, specimens may be 3D printed within trench walls created by milling, ablation, or etching. The 3D printed specimens are usually printed on a glass slide, silicon wafer or piece of silicon wafer, or another substrate. Conductive substrates are preferable for subsequent use in charged particle optical instruments.

The 3D printed AM specimens may be held in place using an extended part of the specimen itself or one or more tabs of material. Since the 3D printing process can produce cantilever-type structures or structures that ultimately contain open holes or spaces, extra tabs of material may be used where needed to provide mass support needed. The tabs of material may vary in size, shape, and dimension; may have a gradient in size, shape and dimension; and may be sufficient in mass to just hold the specimen in place during carriage, shipping, ground, or air transportation. Following the 3D AM process, the FIB can then be used to mill any tabs free for either INLO, EXLO, or EXpressLO methods, or the limited mass tab can be broken free during the INLO, EXLO, or EXpressLO processes. Multiple 3D printed specimens may be printed in a regular (e.g., 5×5, 10×10) or irregular (e.g., 5×10) array, with each 3D printed specimen separated by a spacing of approximately 2-5 times the length of the specimen. A spacing of about 100 micrometers between specimens has been found to work well. The array of 3D printed AM specimens may consist of just one type of specimen or a mixture of two or more 3D printed specimen types. Fiducial marks can also be 3D printed in close proximity to the 3D printed specimen to identity the orientation of the specimen as well as direct use in automated lift out scripting routines used by many FIB vendors. The columns and rows of the specimen arrays may also be printed with identifying marks.

BRIEF DESCRIPTION OF THE DRAWINGS

The foregoing and other objects, features and advantages of the invention will become more readily apparent from the following detailed description of a preferred embodiment of the invention that proceeds with reference to the accompanying drawings, in which:

FIG. 5a is a perspective view of a rectangular cuboid shaped-specimen with a "U-shaped" undercut, formed entirely using an additive manufacturing (AM) or three-dimensional (3D) printing process according to aspects of the invention, that mimics the FIB prepared specimen of FIG. 1h having the same shape.

FIG. 5b is a side elevation view of the U-shaped undercut portion of FIG. 5a.

FIG. 5c is a perspective view of a FIB milling step used on the specimen of FIG. 5a that mimics the end product of the FIB prepared specimen of FIG. 1i.

DETAILED DESCRIPTION

It is understood that these 3D printed AM specimens described can vary slightly in shape and dimensions without altering the intent of the invention.

Figure 4A:
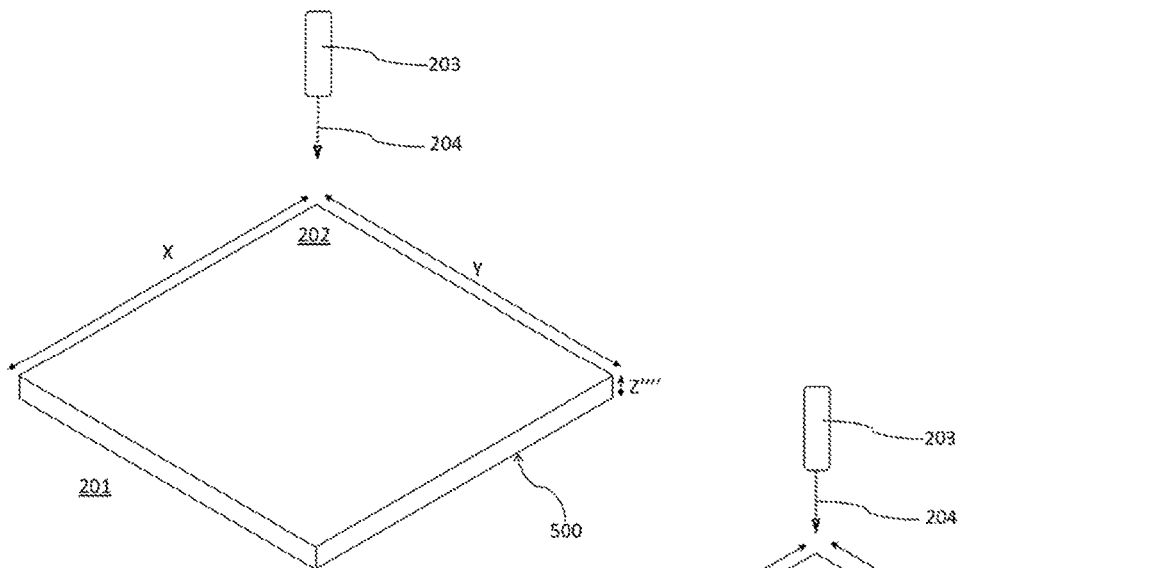
FIGS. 4a-4c are perspective views showing the "additive" manufacturing of a rectangular cuboid-shaped specimen according to aspects of the invention that mimics the end-product of a FIB prepared specimen shown in FIG. 1d having the same shape.

FIG. 4a shows the start of a 3D printed AM processed that is built up above the substrate surface 201 with printed surface 202 using laser focusing optics 203 and scanned laser beam 204. The sample 500 has approximate dimensions X=Y where X and Y are somewhat larger than the specimen to be created, and in this case about 30-35 micrometers. Dimension X and Y need not be equal to each other, however. The exact size of the sample can vary to accommodate the 3D printed specimen size. The height, Z"" in this initial step is only about 1 micrometer but will continue to grow as the sample 500 continues to be printed.

It should be noted that the structures forming the trench floor 205 and sidewalls 206 and the specimen 207 are not yet visible at this early stage in the additive manufacturing process.

Figure 4B:
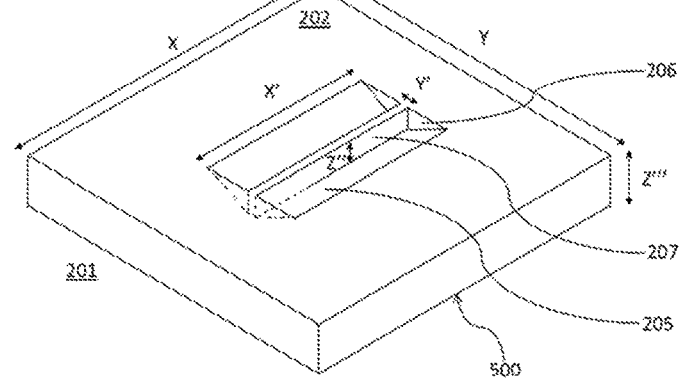

In FIG. 4b, the 3D printing process of sample 500 continues. Sample 500 height Z''' is now about 5 micrometers and the beginnings of trench floor 205 and trench sidewall 206 containing specimen 207 takes shape, mimicking the lower portion of FIB prepared specimen 106 described in FIG. 1d. At this stage, specimen 207 has a height Z'' of only about 1-2 micrometers, X'=20 micrometers in length, and Y' is about 1 micrometer thick.

Figure 1A:
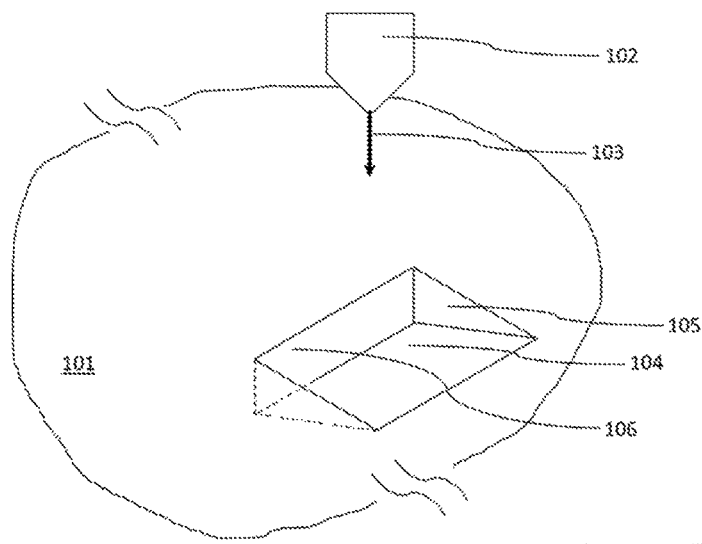
FIGS. 1a-1d are perspective views of steps used to manufacture a rectangular cuboid-shaped specimen using a conventional "subtractive" focused ion beam (FIB) milling process according to aspects of the prior art.
Figure 1B:
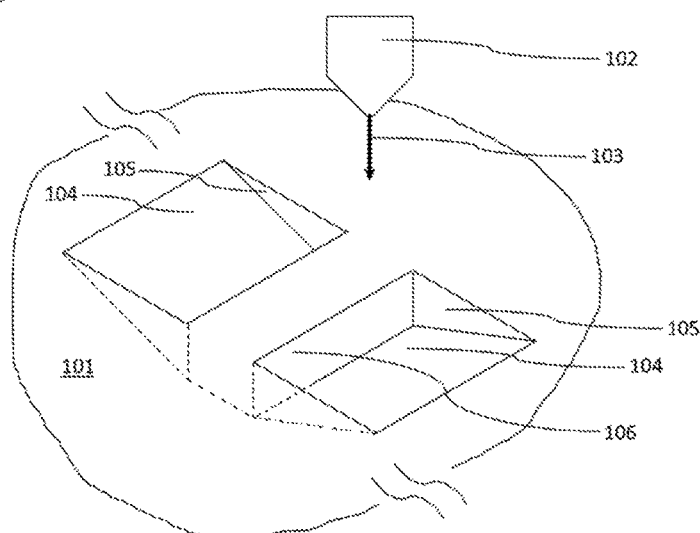
Figure 1C:
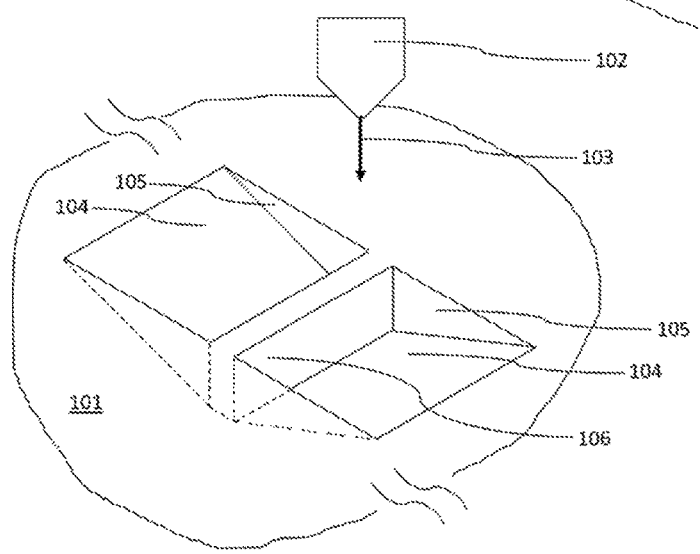
Figure 1D:
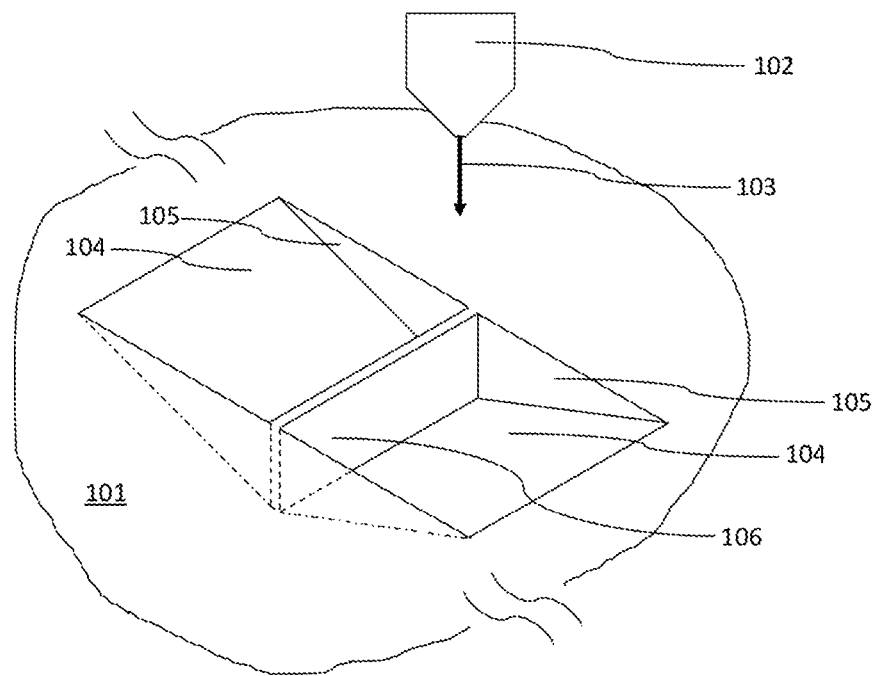
Figure 4C:
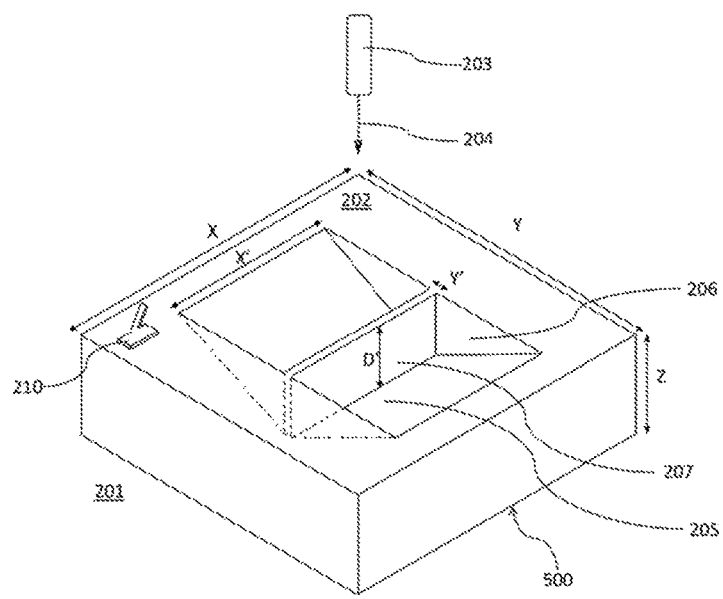

The finished 3D printed sample 500 shown in FIG. 4c mimics the FIB prepared specimen shown in FIG. 1d with the obvious difference that it was built up in seconds using 3D printed technology versus removing material via FIB milling or laser ablation. In FIG. 4c, sample 500 has reached its final height, Z, of about 10-15 micrometers, which is also the distance between substrate surface 201 and sample 500 surface 202. Specimen 207 has final depth, D', of about 7 micrometers. Note that these dimensions can vary as needed to correspond to actual FIB prepared specimens. The logo 210 may be used to orientate the sample or to be used as a fiducial mark for image recognition in vendor specific scripting for subsequent automated specimen processing. Logo or fiducial mark 210 may be produced so that it is inset below surface 202 or raised (e.g., embossed) above surface 202 by about 0.5 micrometers or more as shown, and preferably has an asymmetric form as shown to assist with accurate orientation of the sample. Specimen 207 can be further processed with additional features via 3D printed AM to reduce subsequent FIB milling time as described below. Alternatively, specimen 207 in FIG. 4c may FIB milled for further processing as described below.

Figure 1E:
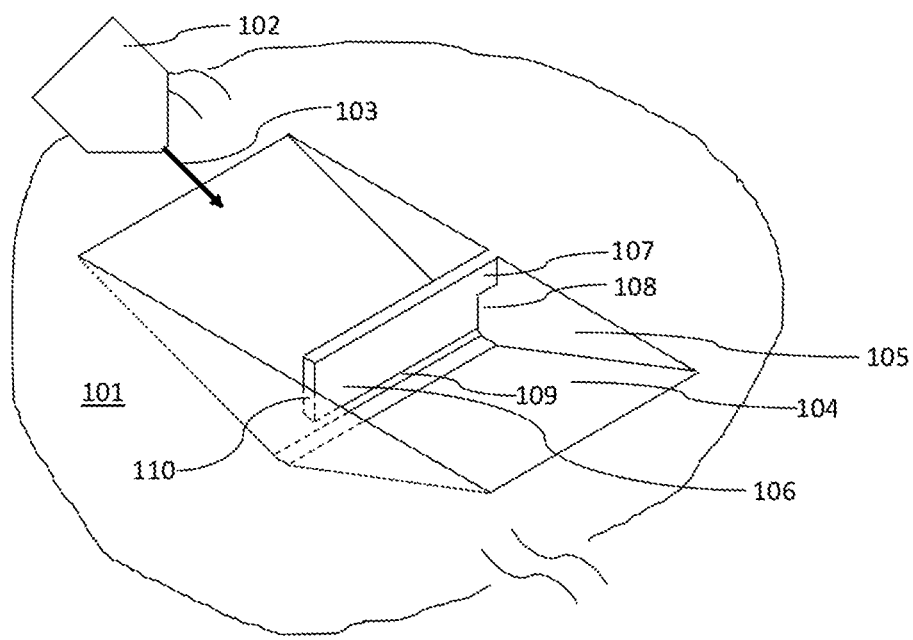
FIGS. 1e-1g are perspective views of steps used to manufacture and manipulate a rectangular cuboid-shaped specimen with a "J-shaped" undercut using conventional "subtractive" FIB milling processes and in situ lift out (INLO) techniques according to aspects of the prior art.
Figure 1F:
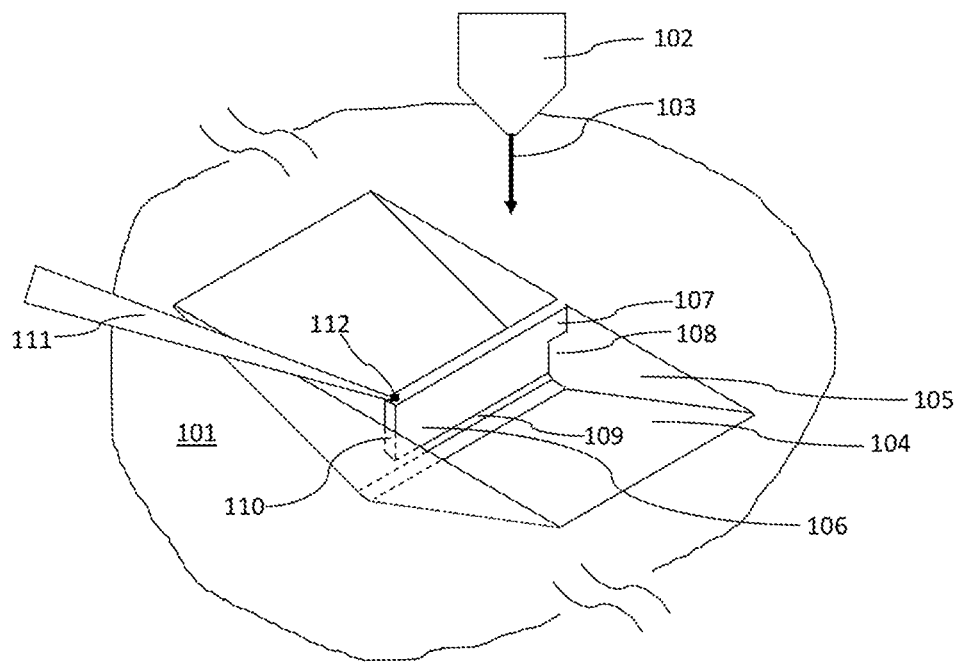
Figure 1G:
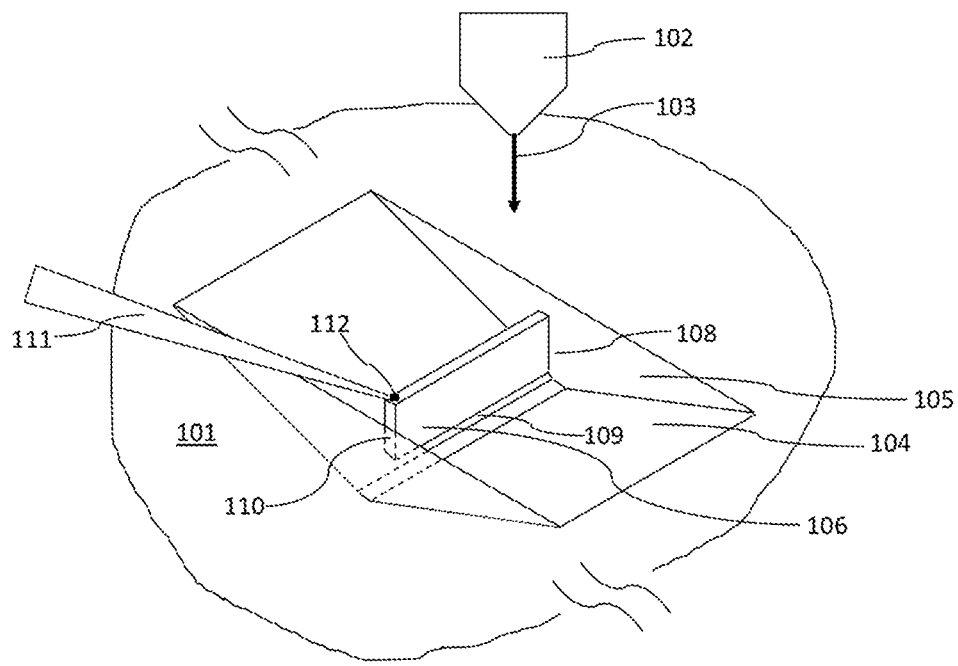
Figure 1H:
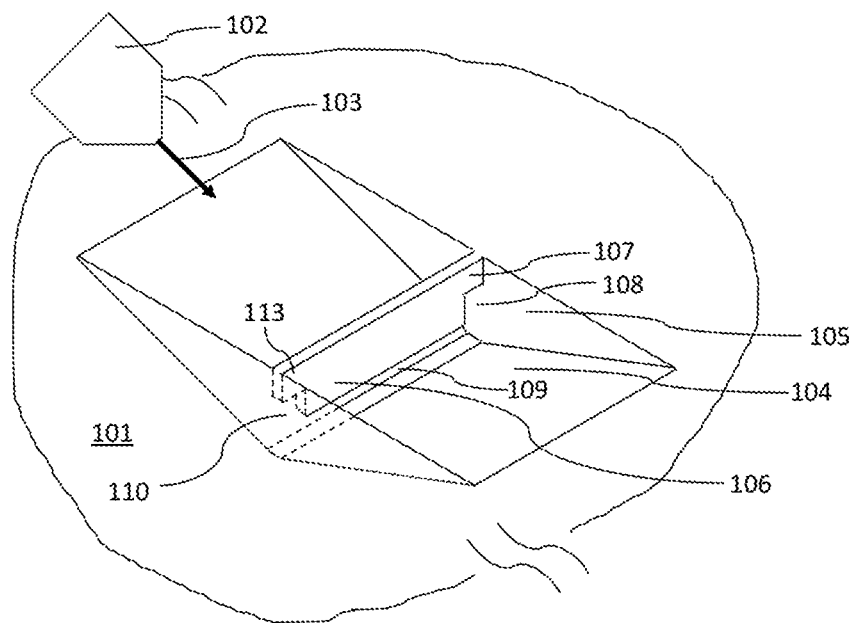
FIG. 1h is a perspective view of a rectangular cuboid-shaped specimen with a "U-shaped" undercut prepared using conventional "subtractive" FIB milling processes according to aspects of the prior art.
Figure 1I:
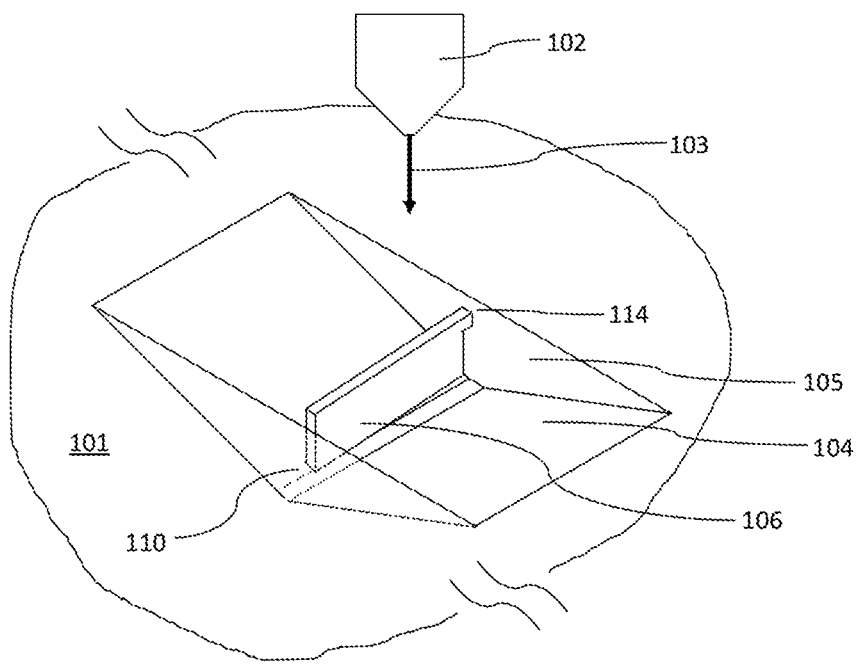
FIG. 1i is a perspective view of a rectangular cuboid-shaped specimen ready for EXLO prepared using conventional FIB milling processes according to aspects of the prior art.
Figure 3A:
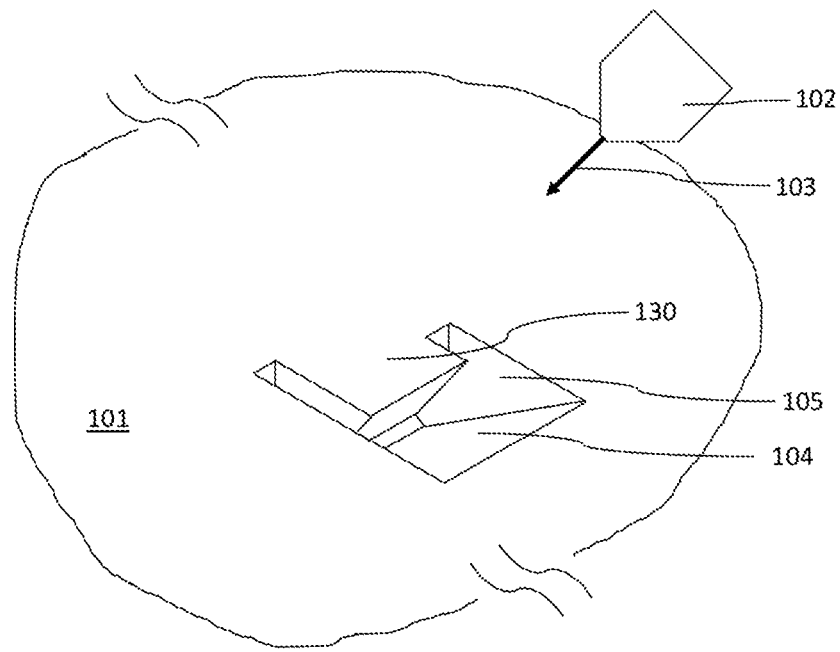
FIGS. 3a-3b are perspective views of the steps used to manufacture a rectangular prism-shaped specimen using conventional "subtractive" FIB processes according to aspects of the prior art.
Figure 3B:
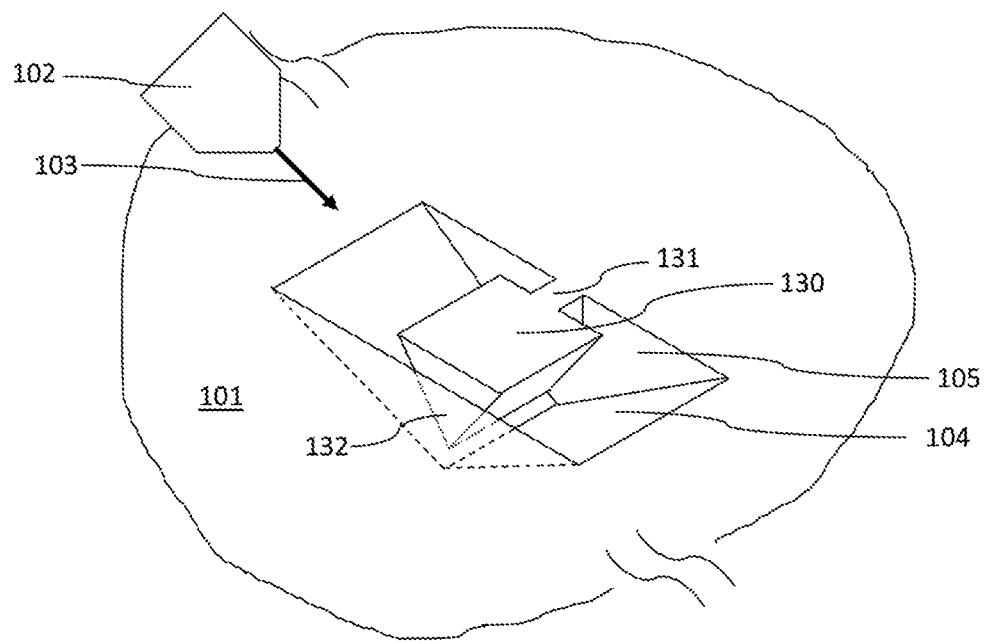
Figure 3C:
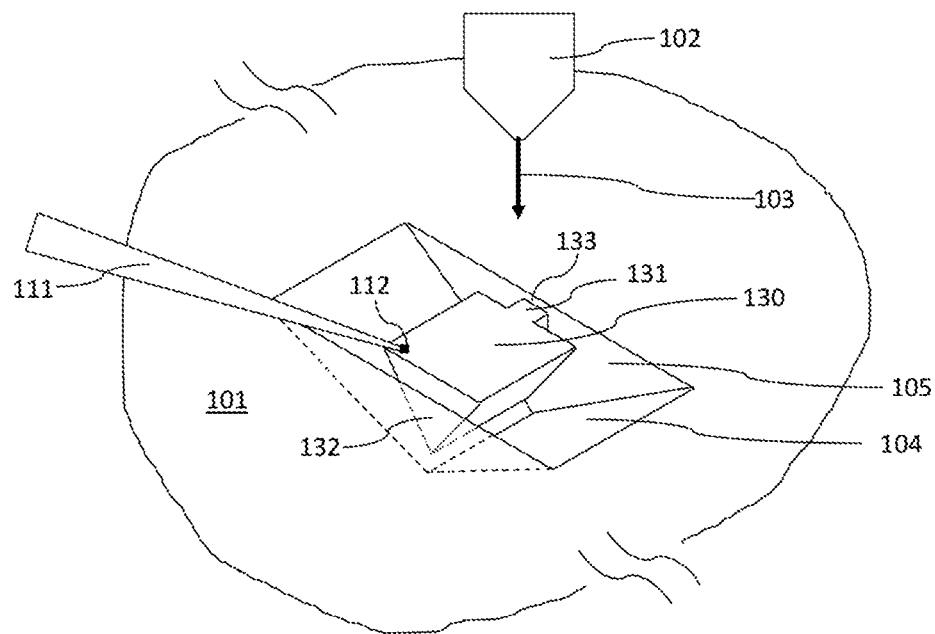
FIG. 3c is a perspective view of the rectangular prism-shaped specimen of FIG. 3b further prepared using conventional FIB processes and manipulated using in situ lift out (INLO) according to aspects of the prior art.
Figure 3D:
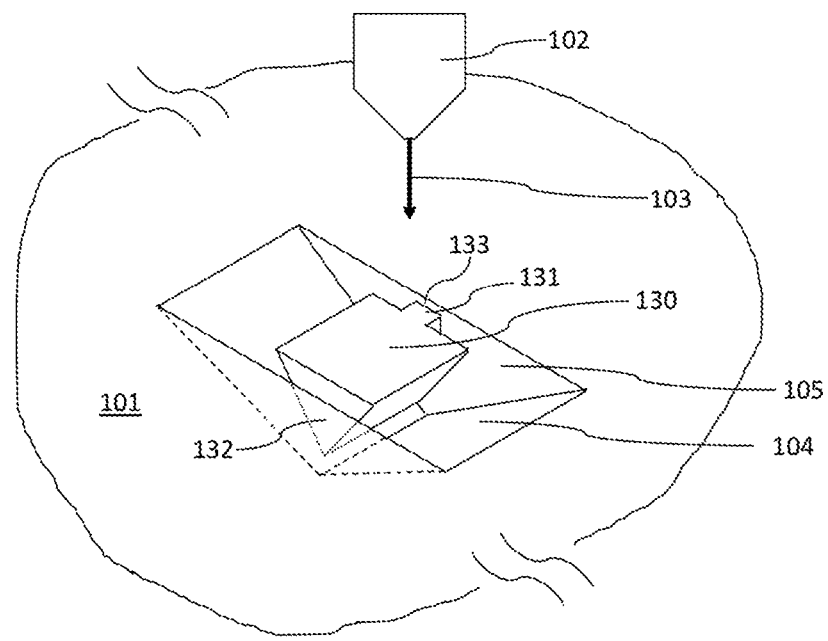
FIG. 3d is a perspective view of the rectangular prism-shaped specimen of FIG. 3b further prepared using conventional FIB processes and ready for EXLO according to aspects of the prior art.
Figure 6A:
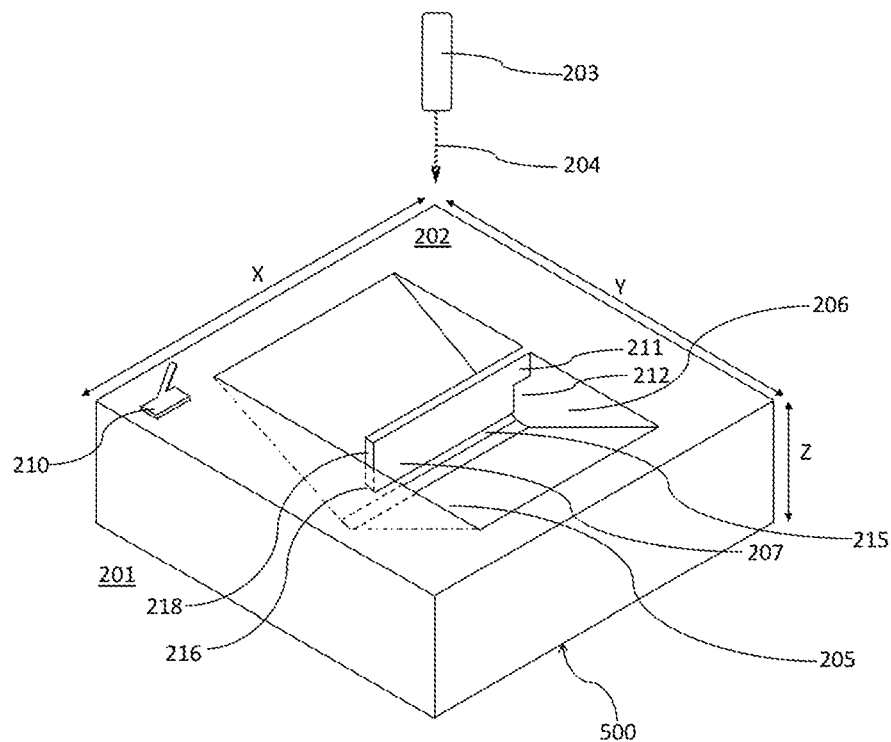
FIG. 6a is a perspective view of a rectangular cuboid-shaped specimen with "J-shaped" undercut, formed entirely using an additive manufacturing (AM) or three-dimensional (3D) printing process according to aspects of the invention, that mimics the FIB prepared specimen of FIG. 1e having the same shape.
Figure 6B:
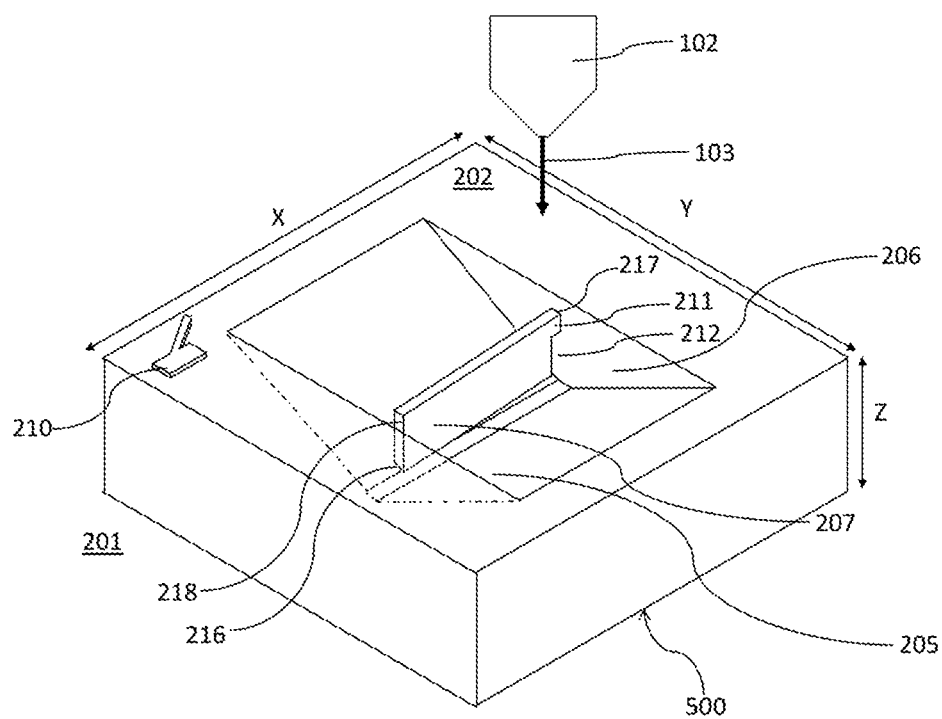
FIG. 6b is a perspective view of a rectangular cuboid-shaped specimen manufactured using teachings of the present invention that is ready for practicing the EXLO extraction method.

In FIG. 5a, 3D printing and AM is used entirely to produce a geometry similar to that of a FIB milled specimen schematically shown in FIG. 1h. In FIG. 5a, the sample 500 3D printed with surface 202 is above substrate surface 201 with trench floor 205 and trench walls 206 holding specimen 207 with material tabs 211 and 213. In this case, specimen 207 has been directly printed to yield empty space around its bottom (215) and edges (212, 214) to resemble the letter "U" such that it is held by two tabs of material 211 and 213. This resulting design mimics the FIB milled specimen in FIG. 1h and reduces subsequent FIB time which may be necessary to ready the specimen for lift out. The cantilevered portion of the specimen may be printed (i) entirely from "bottom-up" where the liquid resist supports the "U" shaped gap until the tabs are printed and the resist is subsequently dissolved away or (ii) from side to side where the specimen is printed out from the tabs. The embossed logo 210 may be used to orientate the sample or to be used as a fiducial mark for image recognition in vendor specific scripting for subsequent automated specimen processing. In FIG. 5a, tabs 211 and 213 are the same thickness as the sample (i.e., dimension Y' in FIG. 5a), but these tab thicknesses may be necked or reduced in dimension to just a few nanometers to allow subsequent lift out without further FIB processing prior to lift out. The undercut angle given by 216 in FIG. 5a is shown in detail in FIG. 5b which is a cross-section of the bottom of specimen 207. Angle A in FIG. 5b may be 3D printed to be 0 degrees or may be manufactured to resemble an actual FIB prepared specimen (i.e., angle A may be about 45 degrees). FIG. 5c shows 3D printed sample 500 after it has been inserted into the FIB for further ion milling processing using either 3D printed geometry described by FIG. 4c or 5a. In FIG. 5c, the FIB 102 is used to mill specimen 207 in FIG. 5a free from its trenches using beam 103. The asymmetrically prepared specimen 207 with single tab 211 separated by the FIB milled open space 217 is consistent with EXpressLO lift out methods described in the applicant's other patents. In FIG. 6a, 3D printing and AM is used entirely to produce a geometry similar to that of the FIB milled specimen schematically shown in FIG. 1e. In FIG. 6a, the sample 500 is 3D printed with surface 202 above substrate surface 201 and with trench sidewall 206 suspending specimen 207 above the trench floor 205 via tab 211. The cantilevered portion of the specimen may be printed (i) entirely from "bottom-up" where the liquid resist supports the gap or lack of printed material until the tabs are printed and the resist is subsequently dissolved away or (ii) from side to side where the specimen is printed out from the tabs. The logo or fiducial mark 210 is shown embossed on surface 202. In FIG. 6a specimen 207 has empty space around its bottom 215 and one side 218 that resembles a mirror image of the letter "J" such that it is held by one tab of material 211 with free space 212 under it. Manufacturing and the design of space under and around specimen 207 further reduces FIB time which may be necessary to ready the specimen for lift out. The bottom geometry of specimen 207 is given by 216 as per FIG. 5b. Specimen 207 defined by FIG. 6a is ready for further FIB milling for subsequent INLO lift out similar to that shown by FIGS. 1f-1g. In addition, sample 500 can be moved to the FIB vacuum chamber and milled for EXLO methods as shown in FIG. 6b where tab 211 is FIB milled free via FIB tool 102 and beam 103 to create free space 217 creating an asymmetric specimen 207 for EXpressLO methods lift out and manipulation.

Figure 2A:
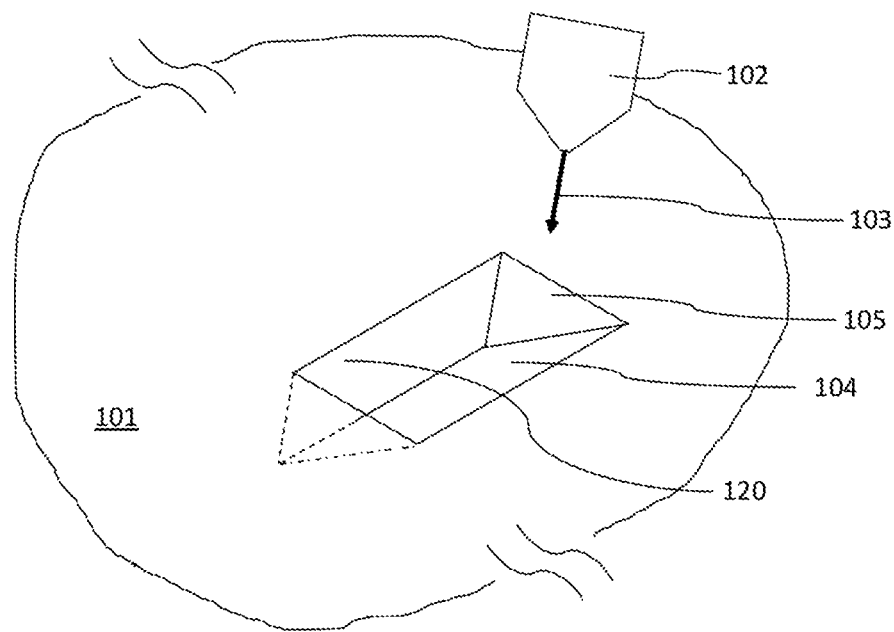
FIGS. 2a-2d are perspective views of the steps used to manufacture and manipulate a triangular prism-shaped specimen using conventional "subtractive" FIB milling processes and using in situ lift out (INLO) according to aspects of the prior art.
Figure 2B:
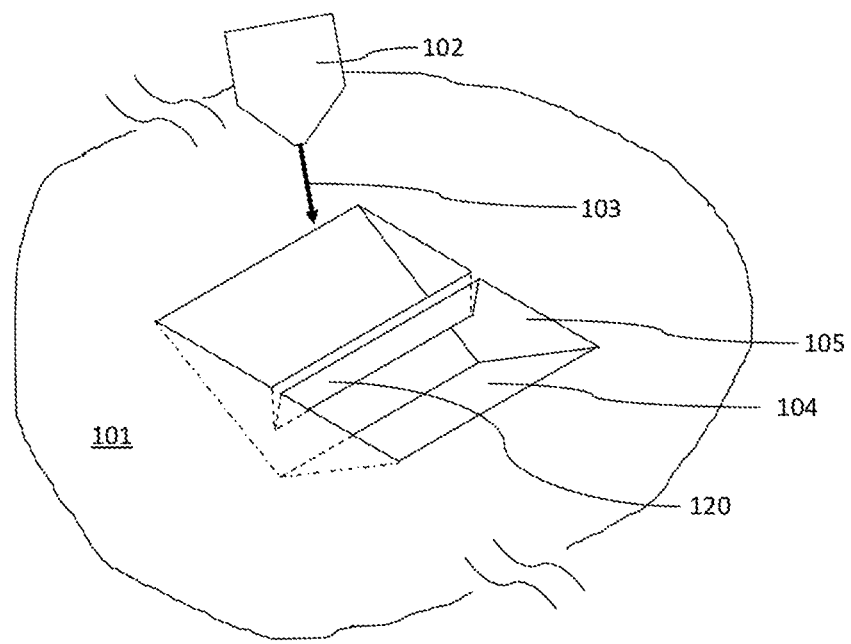
Figure 2C:
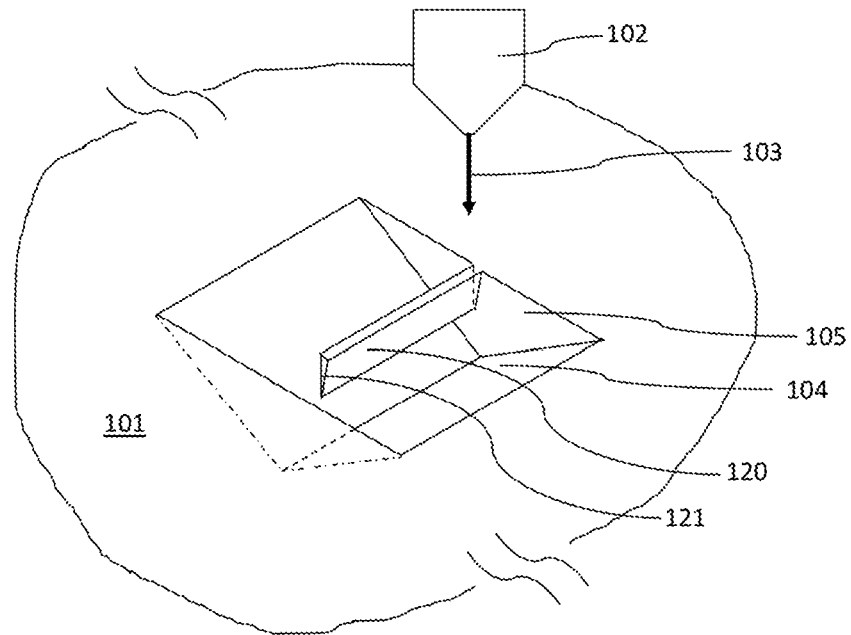
Figure 7A:
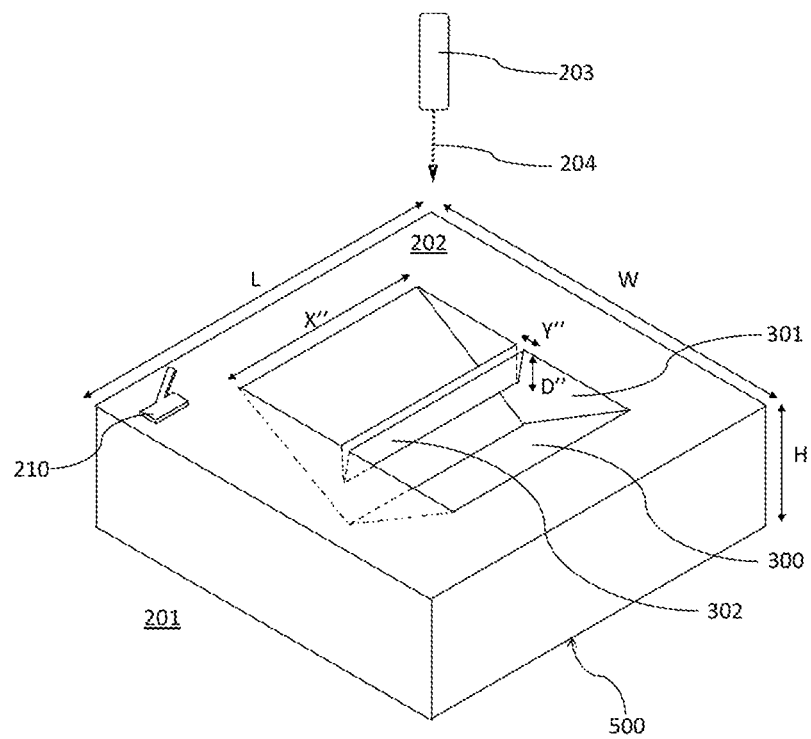
FIGS. 7a-7b are perspective views of a triangular prism-shaped specimen, formed entirely using an additive manufacturing (AM) or three-dimensional (3D) printing process according to aspects of the invention, that mimics a FIB prepared specimen (FIGS. 2b-2c) of the same shape.

FIG. 7a shows 3D printed AM processed specimen 302 within sample 500, having sample top surface 202, that is built up above the substrate surface 201. Sample 500 has approximate dimensions L=W where L and W are somewhat larger than the specimen to be created, and in this case is about 50 micrometers. The exact size of the sample can vary to accommodate the 3D printed specimen size and L need not be equal to W. The height, H, from the substrate surface 201 to the top of the sample surface 202 is about 10 micrometers but can vary depending on the specimen size. The trench floor 300 and sidewalls 301 mimic the FIB trench floor 104 and sidewall 105 as in FIG. 2c. Specimen 302 has dimensions of X"~40 micrometers in length, Y"~1 micrometer thick, and D"~5 micrometers deep. The cantilevered portion of the specimen may be printed (i) entirely from "bottom-up" where the liquid resist supports the gap or lack of printed material until the tabs are printed and the resist is subsequently dissolved away or (ii) from side to side where the specimen is printed out from the tabs. These dimensions can vary as needed to correspond to conventional FIB prepared specimens. The logo 210 may be used to orientate the sample or to be used as a fiducial mark for image recognition in vendor specific scripting for subsequent automated specimen processing. Logo or fiducial mark 210 may be produced so that it is inset below surface 202 or raised (e.g., embossed) about 0.5 micrometers above surface or more 202 as shown. Specimen 302 can be further processed with additional features via 3D printed AM to reduce subsequent FIB milling time as shown below.

Figure 2D:
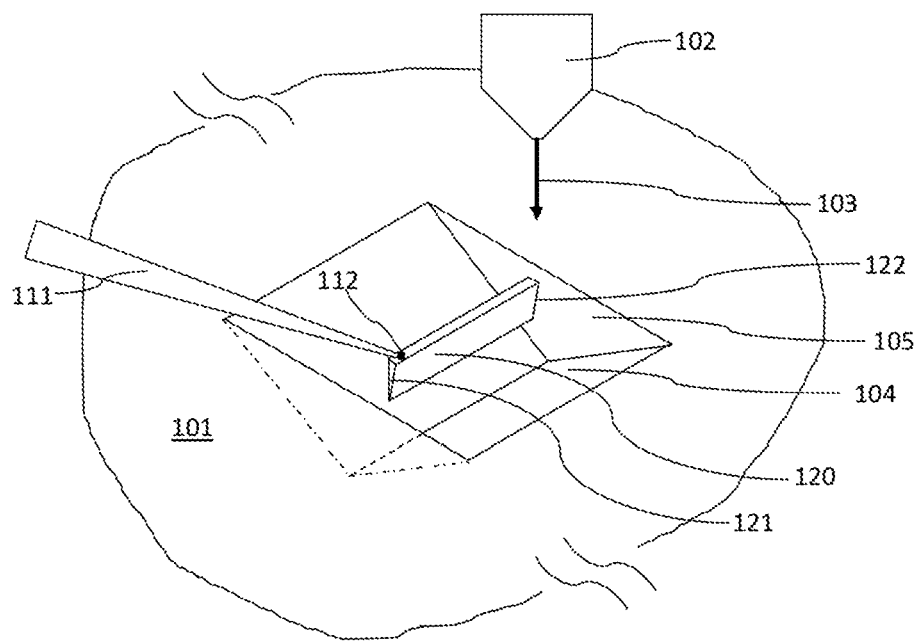
Figure 7B:
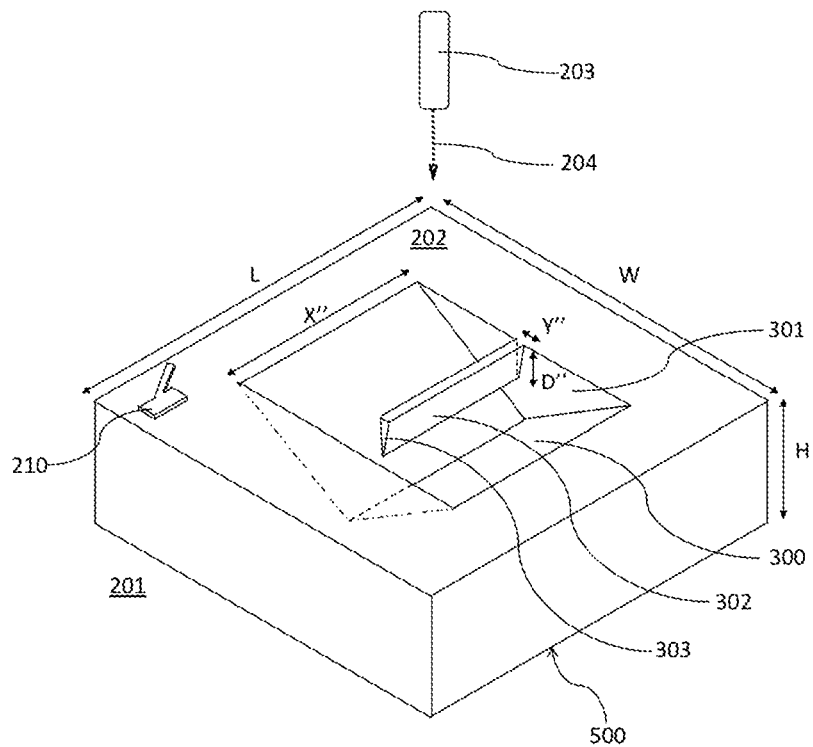

The sample 500 shown schematically in FIG. 7b is nearly identical to FIG. 7a, except the 3D printed specimen 302 is cantilevered leaving edge 303 away from trench sidewall 301. Printing the specimen with cantilever edge 303 saves subsequent FIB time during the lift out process as described by FIG. 2d. The cantilevered portion of the specimen may be printed (i) entirely from "bottom-up" where the liquid resist supports the gap or lack of printed material until the tabs are printed and the resist is subsequently dissolved away or (ii) from side to side where the specimen is printed out from the tabs.

Figure 8A:
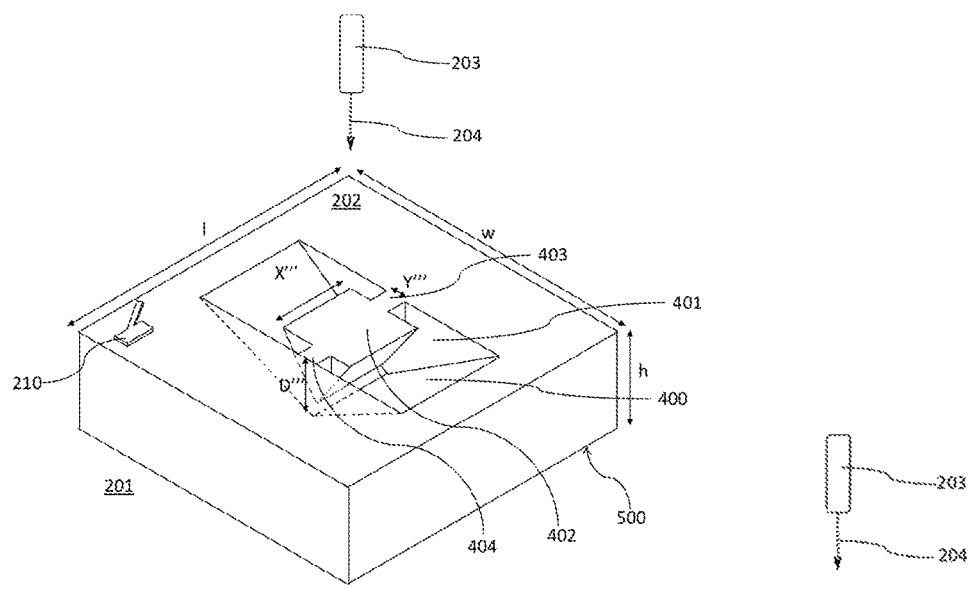
FIG. 8a is a perspective view of a 3D-printed AM rectangular prism-shaped specimen that mimics a FIB prepared specimen of the same shape having two tabs of material attached to the trench.

FIG. 8a is a schematic diagram of a 3D printed AM produced sample 500 that is similar in geometry to the FIB produced version in FIG. 3b. The sample surface 202 is built above substrate surface 201. The sample has approximate dimensions l=w where l and w are somewhat larger than the specimen to be created, and in this case is about 60 micrometers. The exact size of the sample can vary to accommodate the 3D printed specimen size and sample length l need not be equal to sample width w. The sample height, h, from the substrate surface 201 to the top of the sample surface 202 is about 30 micrometers but can be larger and may vary depending on the specimen size. The trench floor 400 and sidewalls 401 mimic the FIB trench floor 105 and sidewalls 105 as in FIG. 3b. The 3D printed wedge-shaped rectangular prism specimen 402 with added tabs 403 and 404 in FIG. 8a is attached to trench sidewalls 401. Specimen 421 has dimensions of about X'''=20 micrometers square, Y''' is about 1-5 micrometers thick, and D''' is about 20 micrometers deep. These dimensions can vary as needed to correspond to conventional FIB prepared specimens. The logo 210 may be used to orientate the sample or to be used as a fiducial mark for image recognition in vendor specific scripting for subsequent automated specimen processing. Logo or fiducial mark 210 may be produced so that it is inset below surface 202 or raised (e.g., embossed) about 0.5 micrometers or more above surface 202 as shown. Specimen 402 can be further processed with additional features via 3D printed AM to reduce subsequent FIB milling time as shown below.

Figure 8B:
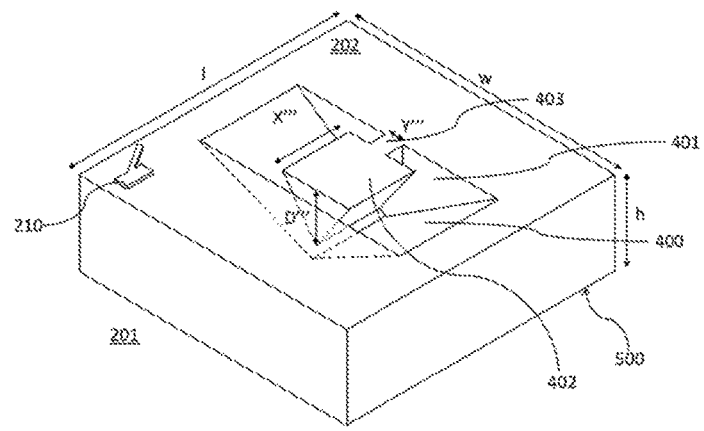
FIG. 8b is a perspective view of a rectangular prism-shaped specimen, formed using an additive manufacturing (AM) or three-dimensional (3D) printing process according to aspects of the invention, that mimics a FIB prepared specimen (FIG. 3b) of the same shape having one material tab attached to the trench.

FIG. 8b is a similar version to 3D printed sample depicted in FIG. 8a, except that the specimen 402 is AM manufactured via laser 203 and beam 204 with only one tab 403 designed to hold specimen 402 against sidewall trench 401. 3D printing only one material tab 403 saves subsequent FIB processing time shown below. The geometry shown by the AM processed sample in FIG. 8b is similar to the FIB milled specimen shown in by FIG. 3b.

Figure 8C:
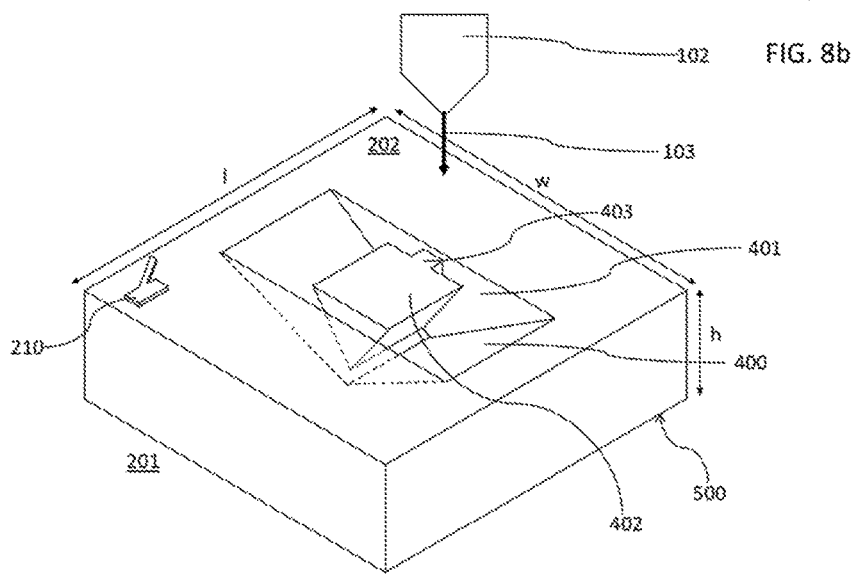
FIG. 8c is a perspective view of a rectangular prism-shaped specimen, formed using an additive manufacturing (AM) or three-dimensional (3D) printing process according to aspects of the invention, that mimics a FIB prepared specimen (FIG. 3d) of the same shape where a portion of the tab of material has been subsequently FIB milled away.

FIG. 8c shows a 3D printed wedge-shaped rectangular prism specimen 402 similar to that shown in FIG. 8a or FIG. 8b after inserted into the FIB vacuum chamber and after part of tab 403 and all of tab 404 has been FIB milled free via FIB tool 102 and beam 103. This geometry specimen is typically used for plan view specimens and the tab provides for asymmetry so that EXLO or ExpressLO methods may be performed.

Figure 9:
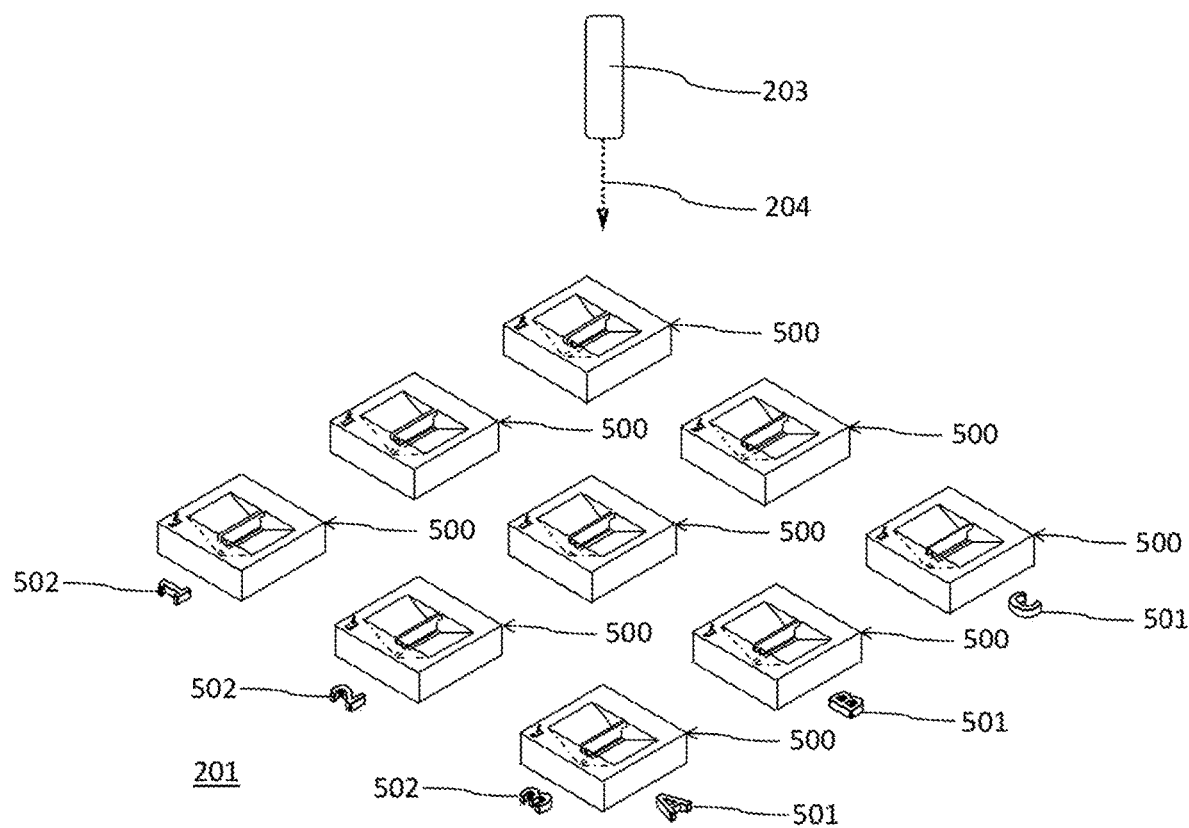
FIG. 9 is a schematic diagram of an array of specimens formed using 3D-printing AM techniques according to aspects of the present invention.

FIG. 9 is a schematic diagram of an array of 3D printed AM specimens. Each 3D printed sample 500 may be comprised of any specimen type described by FIGS. 4-8. The array may be regular (i.e., 3×3, 5×5, or 10×10) or irregular (i.e., 3×5). Each sample may be 3D printed by AM at sufficient spacing (e.g., approximately 50-100 micrometers or more) between samples to allow unimpeded lift out for sufficient repetition for teaching, training, execution, and practice to develop proficiency with different lift out procedures. The 3D printed specimens depicted in FIGS. 4-8 can be used for either in situ lift out (INLO), micro-sampling, ex situ lift out (EXLO), or EXpressLO lift out methods. Numbering or lettering or other marks 501 and 502 may be 3D printed near each column or row of samples, or next to each individual sample, for easy identification of the samples. The height of the marks 501, 502 from surface 201 may be about 0.5 micrometers up to the height of each sample (about 10 micrometers or more). Each mark may also be 3D printed onto each sample 500 itself.

Figure 10:
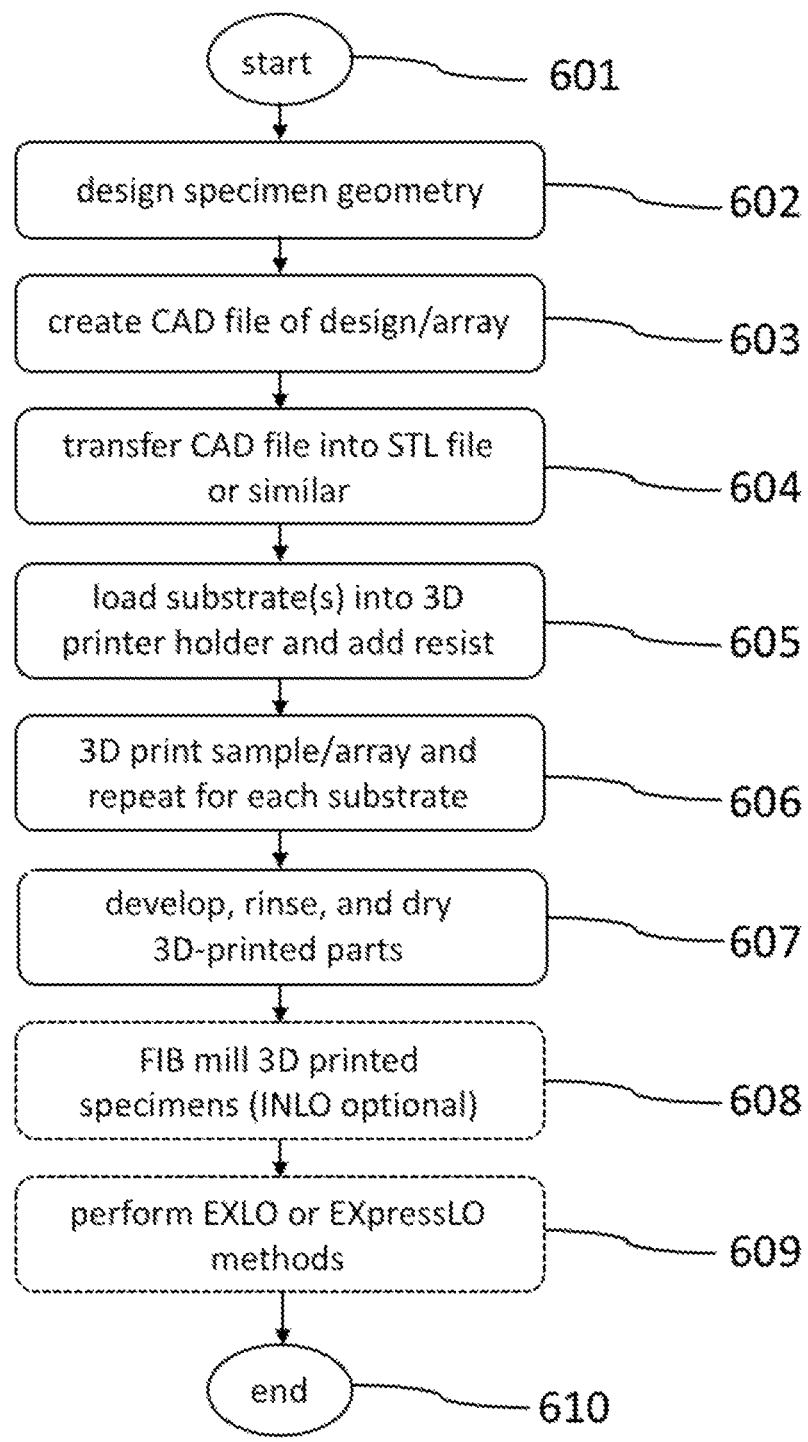
FIG. 10 is a flow chart process of the 3D-printing method for specimens according to aspects of the invention.

The 3D printing AM process of making specimens for teaching, training, and practice is described in FIG. 10. The process starts at block 601 and a specimen geometry is designed in block 602 as with any of the geometries described in FIGS. 4-9. Then a computer aided design (CAD) model is created in block 603 and transferred into a stereolithography (STL) file or similar file in block 604 that is readable by the 3D printer and computer processor. One or more substrates are loaded into the 3D printer holder and resist is deposited onto the substrate in block 605. A single sample or sample array is 3D printed on each substrate in block 606. After the 3D printing process, the samples are developed, rinsed, and dried as per block 607. The substrate containing a sample or sample array is loaded into the FIB vacuum chamber for final FIB milling if needed and to perform optional INLO methods (block 608). After FIB milling (if needed) the sample(s) can be mounted into an EXLO system for EXLO or EXpressLO manipulation in block 609. The process ends in block 610 after all desired lift outs are completed.

Having described and illustrated the principles of the invention in a preferred embodiment thereof, it should be apparent that the invention can be modified in arrangement and detail without departing from such principles. Other materials and processes may be used. I claim all modifications and variation coming within the spirit and scope of the following claims.

What is claimed is:

1. A method for preparing a low-cost microscopy or microanalysis specimen used for training users in lift out techniques for site-specific examination of high-cost specimens, the method comprising:
    building up a sample from a substrate surface using additive manufacturing;
    building up trench walls within the sample that frame a trench using additive manufacturing; and
    building up a micro-lift-out specimen between the trench walls using additive manufacturing.

2. The method of claim 1, wherein the specimen has a shape taken from the group consisting of a lamella, a rectangular cuboid, a triangular prism, and a regular prism.

3. The method of claim 1, wherein the step of building up the specimen between the trench walls using additive manufacturing includes forming a "U-shaped" undercut beneath the specimen so that a bottom edge of the specimen is spaced from a floor of the trench.

4. The method of claim 1, wherein the step of building up the specimen between the trench walls using additive manufacturing includes forming a "J-shaped" undercut beneath the specimen so that a bottom edge of the specimen is spaced from a floor of the trench and one side of the specimen is spaced from one of the trench walls.

5. The method of claim 2, wherein the step of building up the specimen between the trench walls using additive manufacturing includes building the specimen with one side free from the trench walls and an opposite side physically attached to the trench walls.

6. The method of claim 1, further including the step of forming an asymmetric logo or fiduciary mark using additive manufacturing to properly orient the sample during lift-out.

7. The method of claim 6, wherein the asymmetric logo or fiduciary mark is either inset below or embossed above a top surface of the sample.

8. The method of claim 1, further including, and after the step of building up the specimen between the trench walls, milling the sample via focused ion beam milling to break a connection between the sample and the trench walls.

9. The method of claim 1, wherein the step of building up the specimen between the trench walls using additive manufacturing includes forming a bottom edge of the sample with an undercut angle.

10. The method of claim 1, further including the step of building up using additive manufacturing a spaced array of samples with specimens formed within trenches thereof.

* * * * *